United States Patent [19]
Loeffler et al.

[11] Patent Number: 6,159,140
[45] Date of Patent: *Dec. 12, 2000

[54] RADIATION SHIELDED CATHETER FOR DELIVERING A RADIOACTIVE SOURCE AND METHOD OF USE

[75] Inventors: Joseph P. Loeffler, Mountain View; Eric D. Peterson, Fremont; Jon A. Becker, Dublin, all of Calif.

[73] Assignee: Advanced Cardiovascular Systems, Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/024,669

[22] Filed: Feb. 17, 1998

[51] Int. Cl.⁷ ....................................................... A61N 5/00
[52] U.S. Cl. ..................................................................... 600/3
[58] Field of Search .............................................. 600/1–8

[56] References Cited

U.S. PATENT DOCUMENTS

| | | |
|---|---|---|
| 4,661,094 | 4/1987 | Simpson . |
| 4,697,575 | 10/1987 | Horowitz . |
| 4,706,652 | 11/1987 | Horowitz . |
| 4,744,366 | 5/1988 | Jang . |
| 4,748,982 | 6/1988 | Horzewski et al. . |
| 4,762,130 | 8/1988 | Fogarty et al. . |
| 4,763,671 | 8/1988 | Goffinet . |
| 4,771,777 | 9/1988 | Horzewski et al. . |
| 4,771,778 | 9/1988 | Mar . |
| 4,775,371 | 10/1988 | Mueller, Jr. . |
| 4,790,315 | 12/1988 | Mueller, Jr. et al. . |
| 4,815,449 | 3/1989 | Horowitz . |
| 4,861,520 | 8/1989 | van't Hooft et al. . |
| 4,936,823 | 6/1990 | Colvin et al. . |
| 4,940,064 | 7/1990 | Desai . |
| 4,969,863 | 11/1990 | van't Hooft et al. . |
| 4,976,720 | 12/1990 | Machold et al. . |
| 4,983,167 | 1/1991 | Sahota . |
| 4,994,560 | 2/1991 | Kruper, Jr. et al. . |
| 4,998,917 | 3/1991 | Gaiser et al. . |
| 5,002,560 | 3/1991 | Machold et al. . |
| 5,015,230 | 5/1991 | Martin et al. . |
| 5,032,113 | 7/1991 | Burns . |
| 5,034,001 | 7/1991 | Garrison et al. . |
| 5,040,543 | 8/1991 | Badera et al. . |
| 5,046,503 | 9/1991 | Schneiderman . |
| 5,059,166 | 10/1991 | Fischell et al. . |
| 5,061,273 | 10/1991 | Yock . |
| 5,084,002 | 1/1992 | Liprie . |
| 5,100,429 | 3/1992 | Sinofsky et al. . |
| 5,133,956 | 7/1992 | Garlich et al. . |

(List continued on next page.)

FOREIGN PATENT DOCUMENTS

| | | |
|---|---|---|
| 0 633 041 A1 | 1/1995 | European Pat. Off. . |
| 0 688 580 A1 | 12/1995 | European Pat. Off. . |
| 0865803 | 3/1997 | European Pat. Off. . |

(List continued on next page.)

OTHER PUBLICATIONS

PCT Serach report PCT/US 99/03327 Mailed Jun. 18, 1999.
PCT Serach report PCT/US 99/03329 mail ed Jun. 18, 1999.
PCT Serach report PCT/US 99/03328 mailed Jun. 18, 1999.

(List continued on next page.)

*Primary Examiner*—Samuel Gilbert
*Attorney, Agent, or Firm*—Blakely Sokoloff Taylor & Zafman LLP

[57] ABSTRACT

A radiation delivery catheter which increases the margin of safety and reduces unintended exposure to radiation dosage during delivery thereof to a target area to reduce the likelihood of the development of restenosis. The catheter includes a shaft comprised of radiation shielding material, to shield the patient and staff from unintended radiation exposure. The catheter further includes a treatment section including a reservoir balloon comprised of radiation trans-parent material, which enables predetermined concentrations of radioactivity in the radiation source to permeate therethrough into the target area in a substantially uniform dosage pattern.

53 Claims, 4 Drawing Sheets

U.S. PATENT DOCUMENTS

| | | |
|---|---|---|
| 5,137,513 | 8/1992 | McInnes et al. . |
| 5,176,617 | 1/1993 | Fischell et al. . |
| 5,176,661 | 1/1993 | Evard et al. . |
| 5,180,368 | 1/1993 | Garrison . |
| 5,195,971 | 3/1993 | Sirhan . |
| 5,199,939 | 4/1993 | Dake et al. . |
| 5,213,561 | 5/1993 | Weinstein et al. . |
| 5,226,889 | 7/1993 | Sheiban . |
| 5,242,396 | 9/1993 | Evard . |
| 5,258,419 | 11/1993 | Rolando et al. . |
| 5,263,963 | 11/1993 | Garrison . |
| 5,267,960 | 12/1993 | Hayman et al. . |
| 5,273,738 | 12/1993 | Matthews et al. . |
| 5,279,562 | 1/1994 | Sirhan et al. . |
| 5,282,781 | 2/1994 | Liprie . |
| 5,295,959 | 3/1994 | Gurbel et al. . |
| 5,295,960 | 3/1994 | Aliahmad et al. . |
| 5,295,995 | 3/1994 | Kleiman . |
| 5,300,281 | 4/1994 | McMillan et al. . |
| 5,302,168 | 4/1994 | Hess . |
| 5,306,246 | 4/1994 | Sahajian et al. . |
| 5,308,356 | 5/1994 | Blackshear, Jr. et al. . |
| 5,320,824 | 6/1994 | Broadack et al. . |
| 5,334,154 | 8/1994 | Samson et al. . |
| 5,350,361 | 9/1994 | Tsukashima et al. . |
| 5,352,199 | 10/1994 | Tower . |
| 5,354,257 | 10/1994 | Roubin et al. . |
| 5,395,333 | 3/1995 | Brill . |
| 5,405,622 | 4/1995 | Vernice et al. . |
| 5,409,495 | 4/1995 | Osborn . |
| 5,411,466 | 5/1995 | Hess . |
| 5,415,664 | 5/1995 | Pinchuk . |
| 5,441,516 | 8/1995 | Wang et al. . |
| 5,447,497 | 9/1995 | Sogard et al. . |
| 5,456,667 | 10/1995 | Ham et al. . |
| 5,458,572 | 10/1995 | Campbell et al. . |
| 5,484,384 | 1/1996 | Fearnot . |
| 5,498,227 | 3/1996 | Mawad . |
| 5,503,613 | 4/1996 | Weinberger . |
| 5,503,614 | 4/1996 | Liprie . |
| 5,507,301 | 4/1996 | Wasicek et al. . |
| 5,507,769 | 4/1996 | Marin . |
| 5,516,336 | 5/1996 | McInnes et al. . |
| 5,540,659 | 7/1996 | Teirstein . |
| 5,542,925 | 8/1996 | Orth . |
| 5,573,508 | 11/1996 | Thornton . |
| 5,573,509 | 11/1996 | Thornton . |
| 5,643,171 | 7/1997 | Bradshaw et al. . |
| 5,653,691 | 8/1997 | Rupp et al. . |
| 5,688,486 | 11/1997 | Watson et al. . |
| 5,730,698 | 3/1998 | Fischell et al. . |
| 5,840,067 | 11/1998 | Berguer et al. . |
| 5,851,171 | 12/1998 | Gasson . |
| 5,910,101 | 6/1999 | Andrews et al. . |
| 5,938,582 | 8/1999 | Ciamacco, Jr. et al. . |

FOREIGN PATENT DOCUMENTS

| | | |
|---|---|---|
| 0801961 | 10/1997 | European Pat. Off. . |
| 0829271 | 3/1998 | European Pat. Off. . |
| 0879614 | 11/1998 | European Pat. Off. . |
| 4 315 002 | 5/1993 | Germany . |
| 4315002 | 8/1994 | Germany . |
| WO 92/17236 | 10/1992 | WIPO . |
| WO 93/04735 | 3/1993 | WIPO . |
| WO 94/25106 | 11/1994 | WIPO . |
| WO 95/19807 | 7/1995 | WIPO . |
| WO 95/26681 | 10/1995 | WIPO . |
| WO96/06654 | 3/1996 | WIPO . |
| WO 96/10436 | 4/1996 | WIPO . |
| WO96/14898 | 5/1996 | WIPO . |
| WO96/19255 | 6/1996 | WIPO . |
| WO98/01185 | 7/1996 | WIPO . |
| WO97/07740 | 3/1997 | WIPO . |
| WO 97/37715 | 10/1997 | WIPO . |
| WO 97/40889 | 11/1997 | WIPO . |
| WO 98/01183 | 1/1998 | WIPO . |
| WO 98/01184 | 1/1998 | WIPO . |
| WO98/01182 | 1/1998 | WIPO . |
| WO98/39052 | 9/1998 | WIPO . |

OTHER PUBLICATIONS

PCT Serach report PCT/US 99/03360 mailed Jun. 17, 1999.

PCT Serach report PCT/US 99/03343 mailed Jun. 17, 1999.

Lindsay, et al., *Aortic Arterisclerosis in the Dog After Localized Aortic X–Irradiation,* Circulation Research, vol. X, Jan. 1962.

Friedman, et al., *Antiatherogenic Effect of Iridium$^{192}$ Upon the Coloesterol–Fed Rabbit,* Journal of Clinical Investigation, 1964.

Friedman, et al., *Effect of Iridium$^{192}$ Radiation on Thromboatherosclerotic Plaque in the Rabbit Aorta,* Arch Path, vol. 80, Sep. 1965.

Hoopes, et al., *Intraoperative Irradiation of the Canine Abdominal Aorta and Vena Cava,* Int'l Journal Radiation Oncology, Biology, Physics, vol. 13, No. 5, May 1987.

Weshler, et al., *Inhibition by Irradiation of Smooth Muscle Cell Proliferation in the De–Endothelialized Rat Aorta,* 21st Meeting—European Society for Radiation Biology, Frontiers of Radiation Biology, 1988.

Dawson, John T., *Theoretic Considerations Regarding Low––Dose Radiation Therapy for Prevention of Restenosis After Angioplasty,* Texas Heart Institute Journal, vol. 18, No. 1, 1991.

Johnson, M.D., et al., *Review of Radiation Safety in the Cardiac Catherization Laboratory,* Catheterization and Cardiovascular Diagnosis, 1992.

Schwartz, M.D. et al., *Effect of External Beam Irradiation on Neointimal Hyperplasia After Experimental Coronary Artery Injury,* Journal of the American College of Cardiology, vol. 19, No. 5, Apr. 1992.

March, M.D., et al. *8–Methoxypsoralen and Longwave Ultraviolet Irradiation Are a Novel Antiproliferative Combination for Vascular Smooth Muscle,* Krannert Institute of Cardiology, Sep. 1992.

Katzen, Barry T., M.D., *Mechanical Approaches to Restenosis in the Peripheral Circulation,* Miami Vascular Institute at Baptist Hospital (Undated).

Hunink, M.D., et al., *Risks and Benefits of Femoropopliteal Percutaneous Balloon Angioplasty,* Journal of Vascular Surgery, vol. 17, No. 1, Jan. 1993.

Weintraub, M.D., et al., *Can Restenosis After Coronary Angioplasty be Predicted From Clinical Variables?,* Journal of the American College of Cardiology, vol. 21, No. 1, Jan. 1993.

Kuntz, M.D., et al., *Generalized Model of Restenosis After Conventional Balloon Angioplasty, Stenting and Directional Atherectomy,* Journal of the American College of Cardiology, vol. 21, No. 1, Jan. 1993.

Haude, M.D., *Quantitiative Analysis of Elastic Recoil After Balloon Angioplasty and After Intracoronary Implantation of Balloon–Expandable Palmaz–Schatz Stents,* Journal of the American College of Cardiology, vol. 21, No. 1, Jan. 1993.

Schwartz, et al., *Differential Neointimal Response to Coronary Artery Injury in Pigs and Dogs, Implications for Restenosis Models,* Arteriosclerosis and Thrombosis, vol. 14, No. 3, Mar. 1994.

Liermann, et al., *Prophylactic Endovascular Radiotherapy to Prevent Intimal Hyperplasia After Stent Implantation in Femoropopliteal Arteries,* CardioVascular and Interventional Radiology (1994).

Weidermann, et al., *Effects of High–Dose Intracoronary Irradiation on Vasomotor Function and Smooth Muscle Histopathology,* Intracoronary Irradiation and Vasomotion, Jan. 1994.

Wagner, et al., *Potential Biological Effects Following High X–Ray Dose Interventional Procedures,* Journal of Vascular and Interventional Radiology, Jan.–Feb. 1994, pp. 71–84.

Wiedermann, M.D., et al., *Intracoronary Irradiation Markedly Reduces Restenosis After Balloon Angioplasty in a Porcine Model,* Journal of the American College of Cardiology, vol. 23, No. 6, May 1994.

Kakuta, M.D., et al., *Differences in Compensatory Vessel Enlargement, No Intimal Formation, Account for Restenosis After Angioplasty in the Hypercholesterolemic Rabbit Model,* Circulation Research, vol. 89, No. 6, Jun. 1994.

Fischell, M.D., et al., *Low–Dose, β–Particle Emission from 'Stent' Wire Results in Complete, Localized Inhibition of Smooth Muscle Cell Proliferation,* Circulation Research, vol. 90, No. 6, Dec. 1994.

Waksman, M.D., et al., *Endovascular Low–Dose Irradiation Inhibits Neointima Formation After Coronary Artery Balloon Injury in Swine: A Possible Role for Radiation Therapy in Restenosis Prevention,* Circulation Research, vol. 91, No. 5, Mar. 1, 1995.

Wiedermann, M.D., *Intracoronary Irradiation Markedly Reduces Neointimal Proliferation After Balloon Angioplasty in Swine: Persistent Benefit at 6–Month Follow–Up,* Journal of the American College of Cardiology, vol. 25, No. 6, May 1995.

Waksmann, M.D., et al., *Intracoronary Radiation Before Stent Implantation Inhibits Neointima Formation in Stented Porcine Coronary Arteries,* Circulation Research, vol. 92, No. 6, Sep. 15, 1995.

Verin, M.D., et al., *Intra–Arterial Beta Irradiation Prevents Neointimal Hyperplasia in a Hypercholesterolemic Rabbit Restenosis Model,* Circulation Research, vol. 92, No. 8, Oct. 15, 1995.

Waksman, M.D., et al., *Intracoronary Low–Dose β–Irradiation Inhibits Neointima Formation After Coronary Artery Balloon Injury in the Swine Restenosis Model,* Circulation Research, vol. 92, No. 10, Nov. 15, 1995.

Hehrlein, C., et al., *Radioactive Stents,* Discoveries in Radiation for Restenosis, Abstract 22 (Jan. 1996).

Fischell, Tim A., M.D., *A Beta–Particle Emitting Radioisotope Stent for the Prevention of Restenosis,* Discoveries in Radiation for Restenosis, Abstract 23 (Jan. 1996).

Li, et al., *A Novel Brachyehtapy Source for Treatment of Coronary Artery Restenosis,* Discoveries in Radiation for Restenosis, Abstract 24 (Jan. 1996).

Waksman, M.D., et al., *Catheter–Based Radiation in Stented Arteries,* Discoveries in Radiation for Restenosis, Abstract 25 (Jan. 1996).

Martin, Louis G., M.D., *Radiation for Peripheral Applications: Technical Aspects,* Discoveries in Radiation for Restenosis, Abstract 27 (Jan. 1996).

Lumsden, M.D., et al., *Restenosis in Peripheral Vascular Disease,* Discoveries in Radiation for Restenosis, Abstract 28 (Jan. 1996).

Schopohl, et al., *Endovascular Irradiation for Avoidance or Recurrent Stenosis After Stent Implantation in Peripheral Arteries—5 Years Follow–Up,* Discoveries in Radiation for Restenosis, Abstract 29 (Jan. 1996).

Waksman, M.D., et al., *Radiation in the Peripheral System at Emory,* Discoveries in Radiation for Restenosis, Abstract 30 (Jan. 1996).

Teirstein, et al., *Catheter–Based Radiation Therapy to Inhibit Restenosis Following Coronary Stenting Discoveries in Radiation for Restenosis,* Abstract 31 (Jan. 1996).

King III, M.D., et al., *Clinical Restenosis Trials Using Beta Energy Radiation,* Discoveries in Radiation for Restenosis, Abstract 32 (Jan. 1996).

Urban, M.D., et al., *Endovascular Irradiation with 90Y Wire,* Discoveries in Radiation for Restenosis, Abstract 33 (Jan. 1996).

Condado, et al., *Late Follow–Up After Percutaneous Transluminal Coronary Angioplasty (PTCA) and Intracoronary Radiation Therapy (ICRT),* Discoveries in Radiation for Restenosis, Abstract 34 (Jan. 1996).

Weldon, Thomas D., *Catheter Based Beta Radiation System,* Discoveries in Radiation for Restenosis, Abstract 35 (Jan. 1996).

van't Hooft, et al., *HDR Afterloader for Vascular Use,* Discoveries in Radiation for Restenosis, Abstract 36 (Jan. 1996).

Fischell, Robert E., et al., *The Radiosotope Stent: Conception and Implementation,* Discoveries in Radiation for Restenosis, Abstract 37 (Jan. 1996).

Popowski, M.D., et al., *Radioactive Wire in a Self–Centering Catheter System,* Discoveries in Radiation for Restenosis, Abstract 38 (Jan. 1996).

Calfee, Richard V., Ph.D., *High Dose Rate Afterloader System for Endovascular Use—Neocardia,* Discoveries in Radiation for Restenosis, Abstract 39 (Jan. 1996).

Smith, Dr. Edward F., III, *Issues on Handling Radioactive Devices to Prevent Restenosis,* Discoveries in Radiation for Restenosis, Abstract 40 (Jan. 1996).

Unterberg, et al., *Reduced Acute Thrombus Formation Results in Decreased Neointimal Proliferation After Coronary Angioplasty,* Discoveries in Radiation for Restenosis—Selected Literature (Jan. 1996).

Schwartz, et al., *Effect of External Beam Irradiation on Neointimal Hyperplasia After Experimental Coronary Artery Injury,* Discoveries in Radiation for Restenosis—Selected Literature (Jan. 1996).

Hehrlein, et al., *Low–Dose RadioactiveEndovascular Stents Prevent Smooth Muscle Cell Proliferation Neointimal Hyperplasia In Rabbits,* collected in Discoveries in Radiation for Restenosis—Selected Literature (Jan. 1996).

Soares, et al., *Measurement of Radial Dose Distributions Around Small Beta Particle Emitters Using High Resolution Radiochromic Foil Dosimetry,* Nuclear Technology Publishing, vol. 47, pp. 367–372 (Undated).

Byhardt, et al., *The Heart and Blood Vessels,* Radiation Oncology: Rationale, Technique, Results, Chapter Thirteen, pp. 277–284 (Undated).

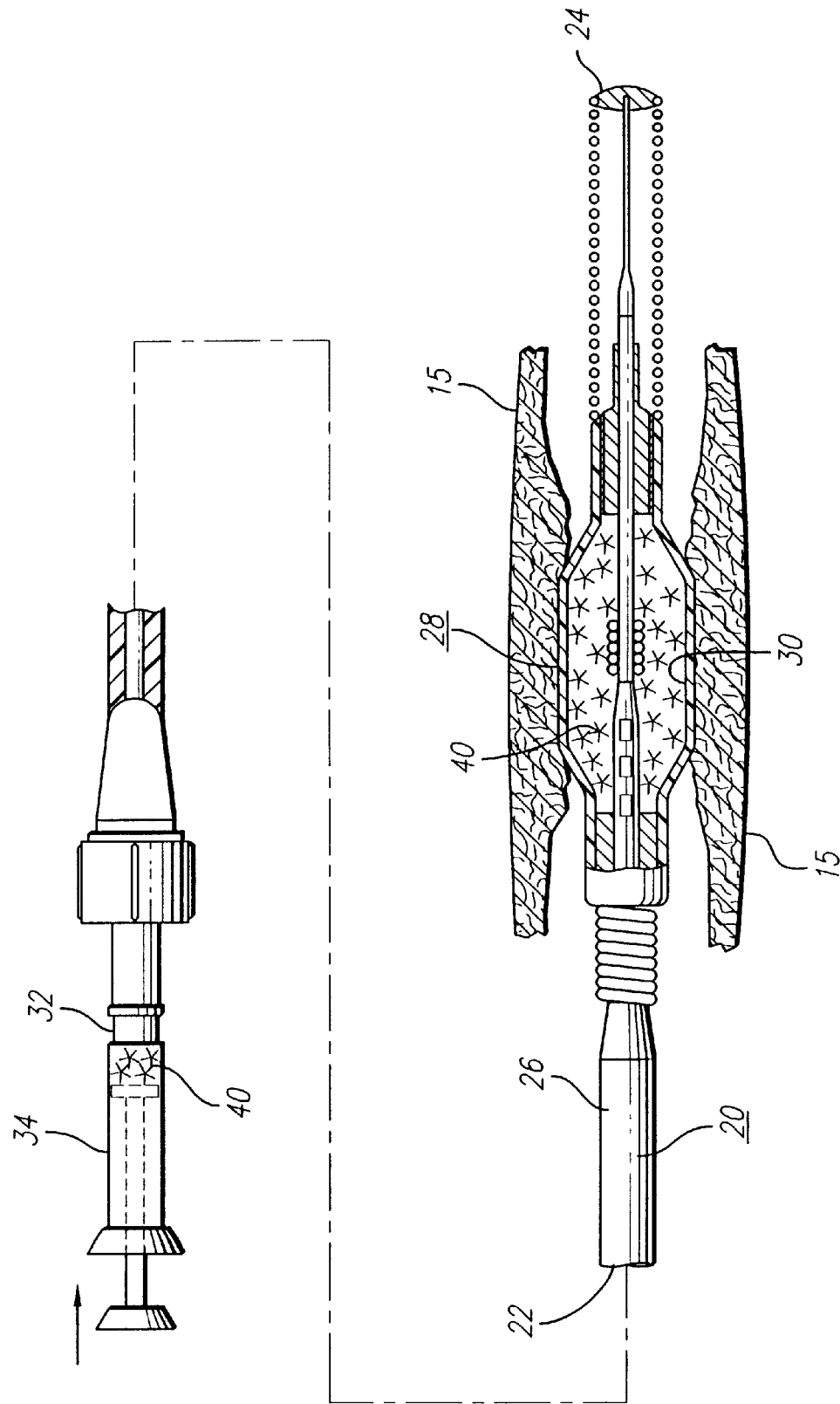

RADIATION SHIELDED CATHETER FOR DELIVERING A RADIOACTIVE SOURCE AND METHOD OF USE

BACKGROUND OF THE INVENTION

1. Field of the Invention

This invention relates to intravascular catheters suitable for delivering a radiation source to a body lumen for example of the kind used in the prevention of restenosis after arterial intervention.

2. Description of the Related Art

In a typical percutaneous transluminal coronary angioplasty (PTCA), for compressing lesion plaque against the artery wall to dilate the artery lumen, a guiding catheter is percutaneously introduced into the cardiovascular system of a patient through the brachial or femoral arteries and advanced through the vasculature until the distal end is in the ostium. A dilatation catheter having a balloon on the distal end is introduced through the catheter. The catheter is first advanced into the patient's coronary vasculature until the dilatation balloon is properly positioned across the lesion.

Once in position across the lesion, a flexible, expandable, preformed balloon is inflated to a predetermined size at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty.

In angioplasty procedures of the kind referenced above, restenosis of the artery often develops which may require another angioplasty procedure, a surgical bypass operation, or some method of repairing or strengthening the area. To reduce the likelihood of the development of restenosis and strengthen the area, a physician can implant an intravascular prosthesis, typically called a stent, for maintaining vascular patency. A stent is a device used to hold tissue in place or to provide a support for a vessel to hold it open so that blood flows freely. Statistical data suggests that with certain stent designs, the restenosis rate is significantly less than the overall restenosis rate for non-stented arteries receiving a PTCA procedure.

A variety of devices are known in the art for use as stents, including expandable tubular members, in a variety of patterns, that are able to be crimped onto a balloon catheter, and expanded after being positioned intraluminally on the balloon catheter, and that retain their expanded form. Typically, the stent is loaded and crimped onto the balloon portion of the catheter, and advanced to a location inside the artery at the lesion. The stent is then expanded to a larger diameter, by the balloon portion of the catheter, to implant the stent in the artery at the lesion. Typical stents and stent delivery systems are more fully disclosed in U.S. Pat. No. 5,514,154 (Lau et al.), U.S. Pat. No. 5,507,768 (Lau et al.), and U.S. Pat. No. 5,569,295 (Lam et al.), which are incorporated herein by reference.

Stents are commonly designed for long-term implantation within the body lumen. Some stents are designed for non-permanent implantation within the body lumen. By way of example, several stent devices and methods can be found in commonly assigned and common owned U.S. Pat. No. 5,002,560 (Machold et al.), U.S. Pat. No. 5,180,368 (Garrison), and U.S. Pat. No. 5,263,963 (Garrison et al.), which are incorporated in herein by reference.

Procedures for the prevention of restenosis after arterial intervention also have employed delivery of a radiation source through the arterial system to the area of the body lumen where the development of restenosis might occur. The radiation source may be delivered by an implanted stent containing a radioactive isotope in the metal which has a short half-life, or a wire having a radioactive source at the distal end that is temporarily placed in the arterial lumen.

However, a compromise had to be made between the shelf life of such radioactive implants and the in vivo efficacious lifetime of the device. If materials with short half lives were used in order to reduce long term radiation exposure of the patient, then the shelf life of the device was unacceptable. If an isotope was used with a long shelf life, then exposure of the patient to radiation was long term.

Radiation treatments using a radioactive wire placed in the artery lumen or inside a catheter were subject to a problem of maintaining a uniform dosage. Since this radioactive wire device is small relative to the artery lumen, the potential exists for it to rest in an off-center position. In this situation, locally high radiation burns were possible on one side of the arterial wall while the other side received a suboptimum dose.

Some radioisotopes considered for use in radiation delivery devices required ion implantation into the device or transmutation of the metal in the device, which would require extra handling and shielding of the device along with the increased cost and complexity of processes like transmutation.

SUMMARY OF THE INVENTION

This invention is directed to a radiation delivery catheter which shields the patient and staff from unintended radiation exposure during treatment for prevention of restenosis.

The present invention attempts to solve the above and other problems associated with radiation delivery catheters.

In an exemplary embodiment of the present invention, the radiation delivery catheter includes a shaft comprised of radiation shielding material, for shielding the patient and staff from unintended radiation exposure. It further includes a treatment section, including an expandable reservoir balloon comprised of non-radiation-shielding material that is radiation transparent for enabling radiation to permeate therethrough into a target area in a substantially uniform pattern.

The radiation delivery system separates the catheter and radioactive source during storage, eliminating the need to compromise between shelf life and in vivo efficacy of radioactive portions of the devices.

A small vial of radioactive liquid contains all of the radioactive source material required, substantially the size of a contrast agent bottle, making storage, handling and shielding more efficient to implement.

A balloon reservoir for delivering the radioactive dosage provides a more uniform dosage pattern to the artery wall.

Separating the device and the radioactive material manufacturing steps enables use of the most efficient and least expensive methods of manufacture of each component, resulting in a less expensive product and improved ability to manufacture.

It is also possible to envision this invention modified for use with a radioactive-tipped wire. In this embodiment, the balloon would be filled with saline or other liquid transparent to radiation, and the radiation source wire would be advanced through a central lumen and placed across the treatment window.

BRIEF DESCRIPTION OF THE DRAWINGS

FIG. 4 is an elevational view, partly in section, depicting a steerable catheter embodying features of the present invention.

DETAILED DESCRIPTION OF THE PREFERRED EMBODIMENTS

Figure 1:
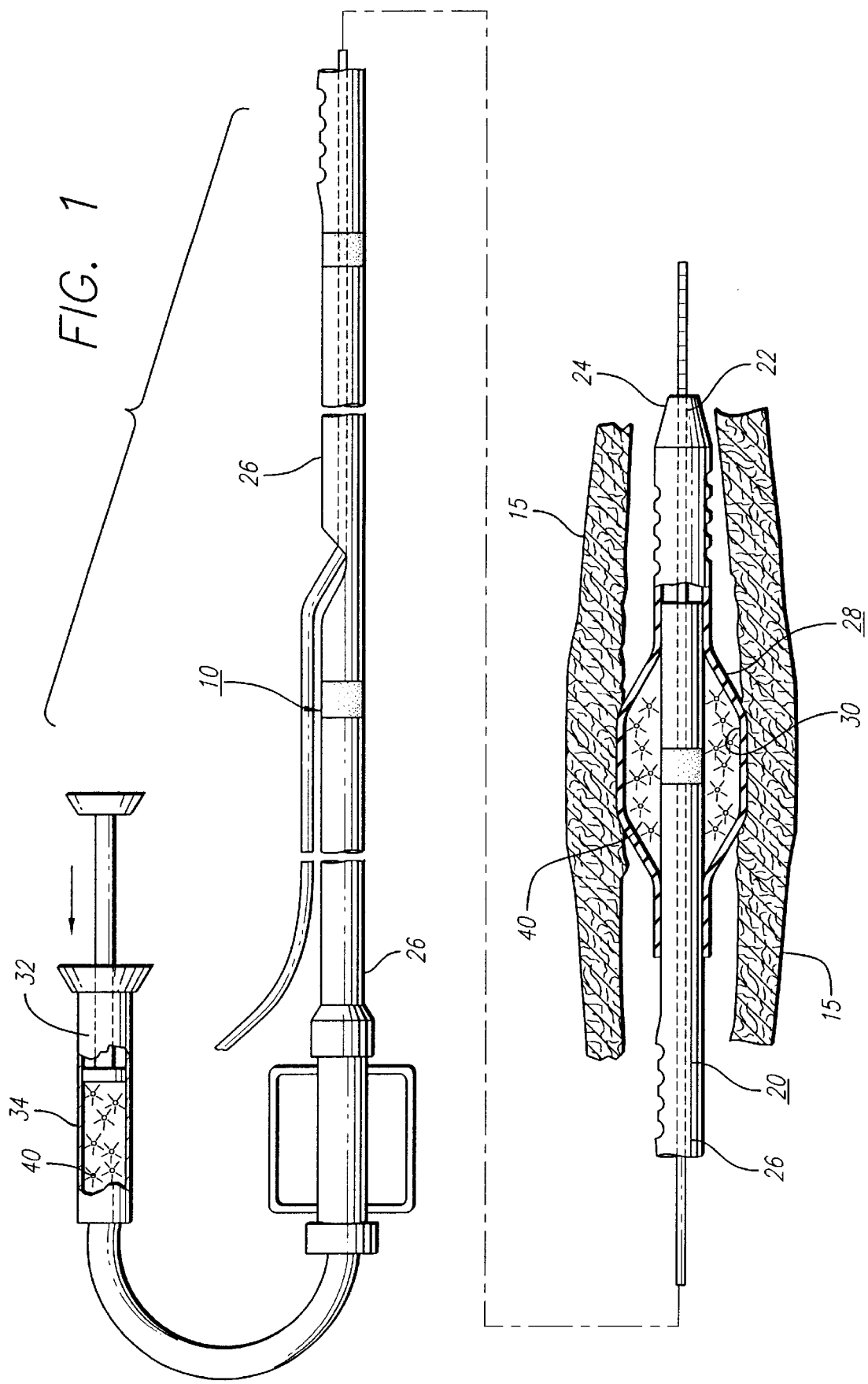
FIG. 1 is an elevational view, partly in section, depicting a perfusion catheter embodying features of the invention.

The present invention provides a catheter which is adapted to deliver a radiation source to a target area in a body lumen, such as a coronary artery, for a period of time. In order to increase the margin of safety and reduce unintended exposure in use of the radiation source, the catheter includes material which shields the patient and staff from unintended radiation exposure. The catheter further includes a treatment section expandable by very low fluid pressures, and comprised of non-radiation-shielding material, adapted to enable predetermined concentrations of radioactivity in the radiation source to permeate therethrough in a substantially uniform pattern, to provide a substantially uniform radiation dosage pattern to the target area. Where different embodiments have like elements, like reference numbers have been used.

As shown in FIGS. 1–4, an intravascular catheter 10 is adapted to deliver a radioactive source to a target area 15 in a body lumen. The radioactive source herein is in the form of a radioactive fluid, adapted to flow through the catheter and into the target area. The term "target area" as used herein refers to that part of the body lumen that has received a PTCA, percutaneous transluminal angioplasty (PTA), atherectomy, or similar procedure to reduce or remove a stenosis, which intervention often leads to the development of restenosis caused, in part, by intimal hyperplasia or the proliferation of smooth muscle cells. The radioactive fluid emits alpha, beta, or gamma radiation particles, has a viscosity which enables it to flow through a small opening, and has a viscosity sufficient to transmit pressure in an open conduit.

Catheter 10 includes an elongated shaft 20, lumen 22 extending through shaft 20, and distal tip 24. Shaft 20 has a shielded section 26 for shielding the body lumen from the radioactive fluid. Shaft 20 may alternatively be comprised of a composite construction, which may constitute a plastic inner tube and a metal outer layer. Depending upon the application, it is preferred that shield section 26 includes substantially all of elongated shaft 20 with the exception of treatment section 28, which is substantially radiation transparent.

Catheter 10 further includes treatment section 28 associated with shaft 20, adapted to treat target area 15 in the body lumen with the radioactive fluid.

Shaft 20 is preferably formed from a base resin material as is known in the art, and shielded section 26 preferably comprises an additive adapted to substantially increase the radiation attenuation capacity of the base resin material. Shaft 20 may be formed in whole or in part from polymers such as polyethylene (PE) or polyethylene terepthalate (PET), or similar polymers, sold by DuPont Company), polyvinyl chloride, nylon, SURYLN®, with shielded section 26 modified to provide radiation shielding. Shaft 20 may for example comprise a polymer, and the additive in shielded section 26 may comprise a material selected from the group which includes boron. The polymer may, during the molten stage of formation, be treated with or have suspended therein a material adapted to block, passivate, or absorb the effects of radiation so that shielded section 26 is substantially radiation opaque. Alternatively, shielded section 26 may be formed at least in part from a material selected from the group of naturally occurring isotopes which include calcium$^{40}$, lead$^{206}$, and sodium$^{23}$, or particles of these isotopes blended into the polymer forming shielded section 26.

Treatment section 28 has a reservoir 30, in fluid communication with shaft lumen 22, and is disposed proximate shaft distal tip 24. Reservoir 30 is adapted to be expandable and to enable preselected concentrations of radioactivity in the radioactive fluid to permeate therethrough into target area 15 of the body lumen, in a substantially uniform pattern, to provide a substantially uniform radioactive dosage pattern to the target area. The term "expandable" as used herein refers to a preformed, non-distensible reservoir 30 which, when it expands, will have a predetermined shape. Reservoir 30 is comprised of a material that is radiation transparent, and is preferably an expandable balloon similar to those used in PTCA or PTA procedures. Reservoir 30 may for example comprise a polymer that is substantially radiation transparent such as PE or PET.

Catheter 10 also includes an adapter 32, in fluid communication with shaft lumen 22 and spaced from reservoir 30, and a device 34 for pressurizing the radioactive fluid, connectable to adapter 32. Pressurizing device 34 is operable at substantially low operating pressure to pressurize the radioactive fluid, such that the radioactive fluid exerts substantially low pressure on reservoir 30 and on the target area. Pressurizing device 34 is preferably shielded from radioactivity, and may further be adapted with an instantaneous radioactive fluid leak detector. Leak detection with pressurizing device 34 may be performed prior to treatment. In a preferred system, pressurizing device 34 will have an operating limit in the range of the lower 0.1% of the distribution of its mean failure modality. Thus, very low fluid pressures are capable of inflating reservoir 30.

Figure 2:
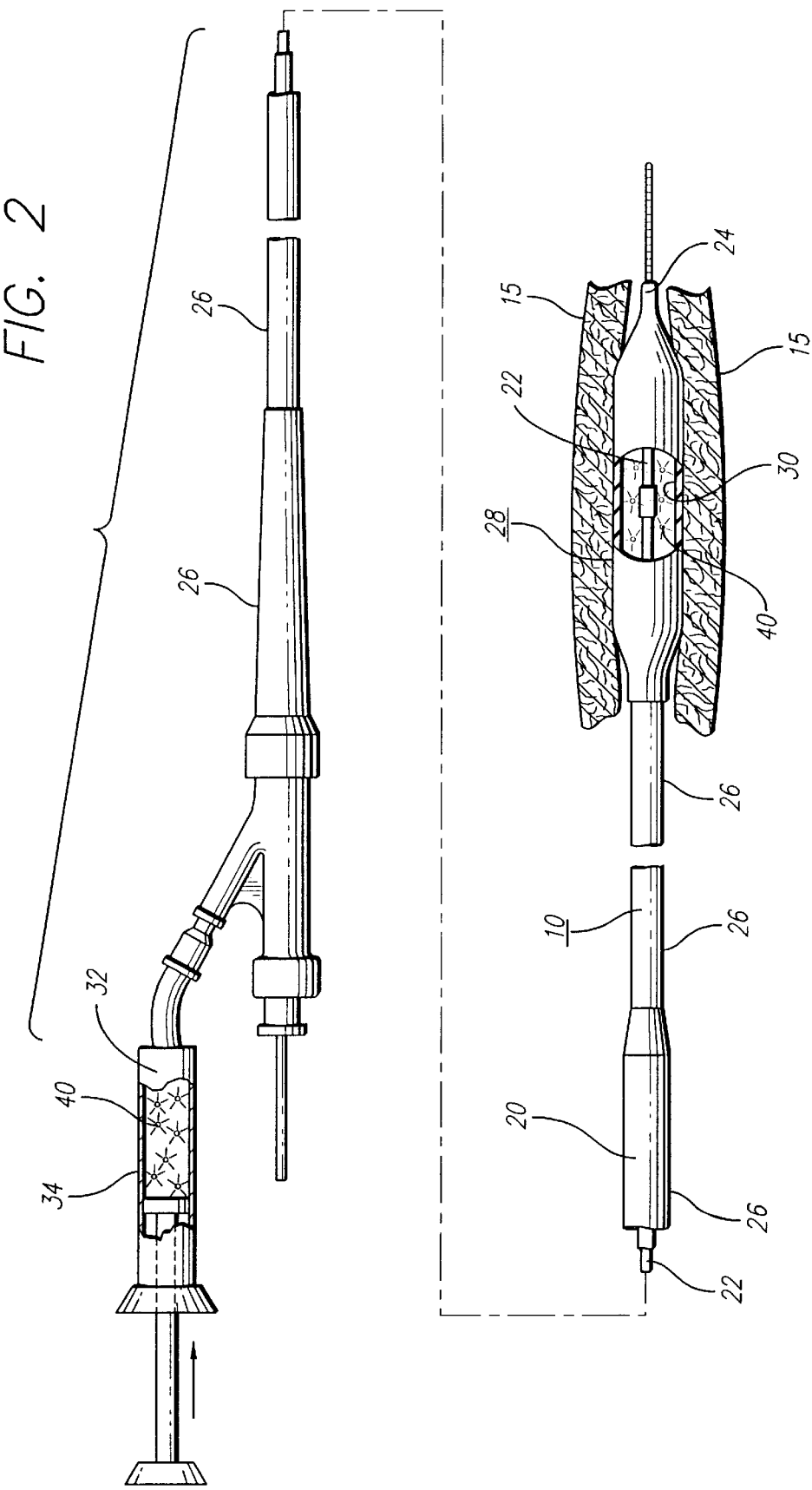
FIG. 2 is an elevational view, partly in section, depicting an over-the-wire catheter embodying features of the invention.
Figure 3:
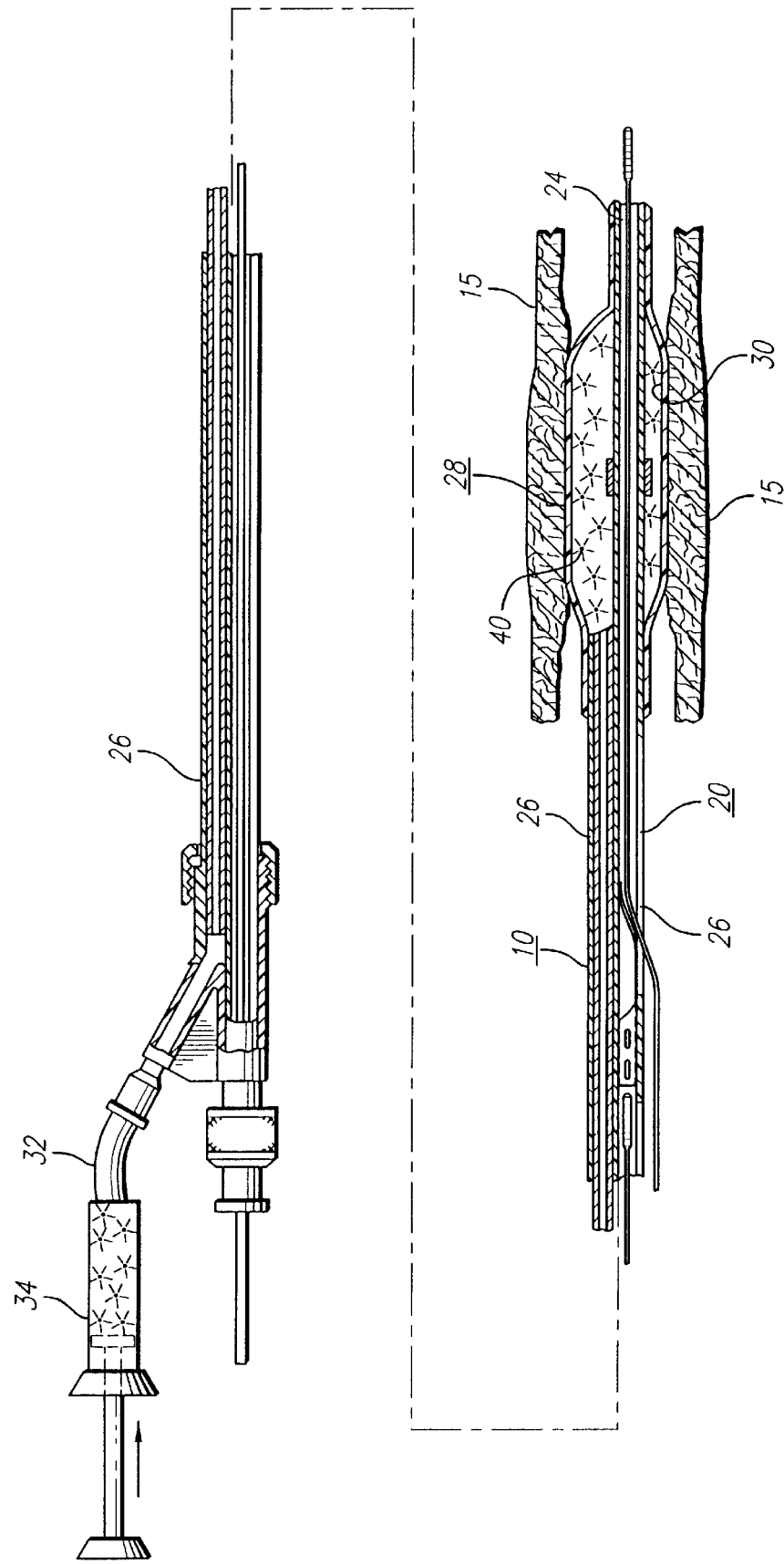
FIG. 3 is an elevational view, partly in section, depicting a rapid exchange catheter embodying features of the present invention.

Catheter 10, for example, may comprise a perfusion catheter as shown in FIG. 1, a non-perfusion over-the-wire catheter as shown in FIG. 2, a rapid exchange catheter as shown in FIG. 3, or a steerable catheter as shown in FIG. 4. Further details regarding perfusion catheters may be found in U.S. Pat. No. 5,516,336, regarding over-the-wire catheters in U.S. Pat. No. 5,480,383, regarding rapid exchange catheters in U.S. Pat. No. 5,458,613, and regarding steerable catheters in U.S. Pat. No. 5,449,343, which are incorporated herein by reference. In the perfusion catheter in FIG. 1, reservoir 30 is disposed proximate distal tip 24. Both the over-the-wire catheter (FIG. 2) and the rapid exchange catheter (FIG. 3) can be adapted to include perfusion capabilities if inflation of reservoir 28 is for a time period necessitating blood flow past the reservoir.

The catheter radiation delivery system may be manufactured, packaged, and sterilized in a manner similar to that which is standard for dilatation products. The target area 15 for irradiation may have had a previous PTCA, PTA, atherectomy, received a stent or otherwise treated with a vascular procedure.

For delivery of a radioactive fluid to target area 15, catheter 10 is advanced to the desired location within the patient's vascular system, such as where the prior vascular procedure has been performed. Reservoir 30 is positioned within target area 15 prior to inflation. Pressurizing device 34 connected to catheter adapter 32 is then operable to generate flow of the radioactive fluid 40 through catheter lumen 22 and into catheter treatment section 28, expanding reservoir 30 into contact with target area 15, and enabling predetermined concentrations of radioactivity in radioactive fluid 40 to penetrate target area 15. Reservoir 30 is left in place in the expanded condition for sufficient time, preferably from about one minute up to about sixty minutes, to allow a sufficient radiation dose to destroy the cells likely to cause development of restenosis. As described, longer inflation times for reservoir 30 necessitates the use of a catheter design having perfusion capabilities.

After the radiation source has been administered to target area 15, radioactive fluid 40 may be withdrawn from reservoir 30 into radiation shielded pressurizing device 34. Catheter 10 is then withdrawn from the location within the patient's vasculature.

Since the radioactive fluid is not injected in catheter 10 until reservoir 30 is positioned within target area 15, and is removed from catheter 10 prior to removal of catheter 10 from the target area, this substantially reduces exposure of the patient and laboratory staff to the radiation source while catheter 10 is in transit to and from the target area.

In use at target area 15, shielded elongated catheter shaft 20 substantially increases the margin of safety and reduces unintended exposure in the use of the radioactive fluid.

As described herein, the catheter assembly will deliver a low dosage of radiation to the body lumen, such as a coronary artery, and is configured to provide the dosage over time. It is preferred that a low dosage of radiation, on the order of 0.1 up to 3.0 curies be the typical radiation level provided to treat, for example, a coronary artery. Preferably, 1.0 to 2.0 curies will provide the proper radiation level.

The radiation dose delivered to a coronary artery should be in the range from about 500 to 3,000 rads in preferably not less than two minutes. The radiation dose can be delivered in less than two minutes, however, it is preferred that a longer time frame be used so that a lower dose can be administered. The dose amounts and radiation exposure times are exemplary and not intended to be limiting. Those skilled in the art will understand that the curie level of the radiation source, the dose level, and exposure time are interrelated and variable, and the optimum parameters will be determined by the particular application. Thus, those skilled in the art will understand that the invention as described herein can be used in any artery or vein and the radiation dose level will necessarily vary for each application.

It is contemplated that different radiation sources can be used, and the preferred radiation sources include iridium$^{192}$, cobalt$^{60}$, vanadium$^{48}$, gold$^{198}$, and phosphours$^{32}$. Further, it is contemplated that the radiation sources emit either alpha, beta, or gamma particles to destroy target cells. The use of alpha-, beta-, and gamma-emitting radiation is well known for treating and killing cancerous cells.

Other modifications can be made to the present invention by those skilled in the art without departing from the scope thereof. The specific dimensions, dosages, times and materials of construction are provided as examples and substitutes are readily contemplated which do not depart from the invention.

What is claimed is:

1. An intravascular catheter for delivering a radioactive source to a target area in a body lumen, comprising:
   an elongated shaft having a shielded section and a treatment section;
   the shielded section for shielding the body lumen from a radioactive source; and
   the treatment section being comprised of a material for enabling radiation from the radioactive source to pass through the treatment section into the target area of the body lumen.

2. The catheter of claim 1, wherein:
   the elongated shaft having a lumen extending therethrough, and a distal tip; and
   the treatment section further having a reservoir disposed proximate the shaft distal tip, the reservoir being in fluid communication with the shaft lumen, adapted to be expandable, enables predetermined concentrations of radioactivity in the radioactive source to permeate therethrough, wherein the radioactive source is in the form of a radioactive fluid, adapted to flow through the shaft lumen and to expand the reservoir into contact with the target area.

3. The catheter of claim 2, wherein the reservoir is formed from a radiation transparent polymer for enabling radiation to transmit therethrough in a substantially uniform pattern to provide a substantially uniform radioactive dosage pattern to the target area.

4. The catheter of claim 2, wherein the reservoir comprises an expandable balloon.

5. The catheter of claim 2, wherein the radioactive fluid has a viscosity which enables the radioactive fluid to flow through openings the size of the shaft lumen.

6. The catheter of claim 2, further comprising an adapter in fluid communication with the shaft lumen and spaced apart from the reservoir; and
   a pressurizing device connected to the adapter, the pressurizing device operable at substantially low operating pressure to pressurize the radioactive fluid such that the radioactive fluid exerts substantially low pressure on the reservoir and hence on the target area.

7. The catheter of claim 6, wherein the pressurizing device has shielding to protect against radioactive emissions from the radioactive source.

8. The catheter of claim 7, wherein the pressurizing device is further adapted with a fluid leak detector to instantaneously detect radioactive fluid leaks.

9. The catheter of claim 2, wherein the radioactive fluid emits alpha, beta, or gamma particles.

10. The catheter of claim 2, wherein the reservoir is disposed proximate the shaft distal tip, and the catheter comprises a perfuision catheter.

11. The catheter of claim 2, wherein the catheter comprises an over-the-wire-catheter.

12. The catheter of claim 2, wherein the catheter comprises a rapid exchange catheter.

13. The catheter of claim 2, wherein the catheter comprises a steerable catheter.

14. The catheter of claim 1, wherein the shaft is formed from a base resin material, and the shielded section further comprises an additive adapted to substantially increase the radiation attenuation capacity of the base resin material.

15. The catheter of claim 14, wherein the base resin material comprises a polymer, and the additive comprises a material selected from the group which includes; boron calcium$^{40}$, lead$^{206}$, sodium$^{23}$, and any combination thereof.

16. The catheter of claim 1, wherein the shaft is comprised of a composite construction.

17. The catheter of claim 16, wherein the shaft composite construction comprises a plastic inner tube coaxial with a metal outer layer.

18. The catheter of claim 1, wherein the shielded section comprises a polymer.

19. The catheter of claim 1, wherein the treatment section is comprised of a substantially radiation transparent polymer.

20. The catheter of claim 1, wherein the shielded section is formed at least in part from a material selected from the group of naturally occurring isotopes which include; calcium$^{40}$, lead$^{206}$, sodium$^{23}$, and blended particles of these isotopes.

21. The catheter of claim 1, wherein the catheter comprises a perfusion catheter.

22. The catheter of claim 1, wherein the catheter comprises an over-the-wire catheter.

23. The catheter of claim 1, wherein the catheter comprises a rapid exchange catheter.

24. The catheter of claim 1, wherein the catheter comprises a steerable catheter.

25. A method of delivering a radioactive source to a target area in a body lumen, comprising:
providing an intravascular catheter, which includes:
an elongated shaft including a shielded section; and
a treatment section comprised of a material for enabling radiation from the radioactive source to pass through the treatment section into the target area;
inserting the catheter shaft in the body lumen until the treatment section is positioned within the target area;
inserting the radioactive source into the treatment section, to emit radiation through the treatment section into the target area;
leaving the treatment section in place for a predetermined period of time to enable radiation from the radioactive source to pass therethrough into the target area;
withdrawing the radioactive source from the treatment section; and
withdrawing the catheter from the body lumen.

26. The method of claim 25, wherein the catheter treatment section further includes a reservoir, adapted to be expandable and to enable predetermined concentrations of radioactivity in the radioactive source to permeate therethrough, the radioactive source being in the form of a radioactive fluid, adapted to flow through the shaft lumen and to expand the reservoir into contact with the target area, and the step of inserting the radioactive source comprises applying pressure to the radioactive fluid to initiate flow through the shaft lumen into the reservoir.

27. The method of claim 25, wherein the catheter shaft includes a lumen extending therethrough, and a distal tip, and the reservoir is disposed proximate the shaft distal end and is in fluid communication with the shaft lumen, the step of applying pressure further comprises applying pressure to the radioactive fluid so as to generate flow thereof through the shaft lumen and to expand the reservoir into contact with the target area.

28. An intravascular catheter for delivering a radioactive source to a target area in a body lumen, comprising:
an elongated shaft having a shielded section and a treatment section;
the elongated shaft having a lumen extending therethrough, and a distal tip;
the shielded section for shielding the body lumen from a radioactive source; and
the treatment section being comprised of a material for enabling radiation from a radioactive source to pass through the treatment section into the target area of the body lumen, the treatment section further having a reservoir, disposed proximate the shaft distal tip, and in fluid communication with the shaft lumen, adapted to be expandable and to enable predetermined concentrations of radioactivity in the radioactive source to permeate therethrough, wherein the radioactive source is in the form of a radioactive fluid, adapted to flow through the shaft lumen and to expand the reservoir into contact with the target area.

29. The catheter of claim 28, wherein the shaft is formed from a base resin material, and the shielded section further comprises an additive adapted to substantially increase the radiation attenuation capacity of the base resin material.

30. The catheter of claim 29, wherein the base resin material comprises a polymer, and the additive comprises a material selected from the group which includes: boron, calcium$^{40}$, lead$^{206}$, sodium$^{23}$, and any combination thereof.

31. The catheter of claim 28, wherein the shielded section comprises a polymer.

32. The catheter of claim 28, wherein the treatment section is comprised of a substantially radiation transparent polymer.

33. The catheter of claim 28, wherein the shielded section is formed at least in part from a material selected from the group of naturally occurring isotopes which include: calcium$^{40}$, lead$^{206}$, sodium$^{23}$, and blended particles of these isotopes.

34. The catheter of claim 28, wherein the catheter comprises a perfusion catheter.

35. The catheter of claim 28, wherein the catheter comprises an over-the-wire catheter.

36. The catheter of claim 28, wherein the catheter comprises a rapid exchange catheter.

37. The catheter of claim 28, wherein the catheter comprises a steerable catheter.

38. The catheter of claim 28, wherein the reservoir is formed from a radiation transparent polymer for enabling radiation to transmit therethrough in a substantially uniform pattern to provide a substantially uniform radioactive dosage pattern to the target area.

39. The catheter of claim 28, wherein the reservoir comprises an expandable balloon.

40. The catheter of claim 28, wherein the radioactive fluid has a viscosity which enables the radioactive fluid to flow through openings the size of the shaft lumen.

41. The catheter of claim 28, further comprising an adapter in fluid communication with the shaft lumen and spaced from the reservoir; and
a pressurizing device connected to the adapter, the pressurizing device operable at substantially low operating pressure to pressurize the radioactive fluid such that the radioactive fluid exerts substantially low pressure on the reservoir and hence on the target area.

42. The catheter of claim 41, wherein the pressurizing device has shielding to protect against radioactive emissions from the radioactive source.

43. The catheter of claim 42, wherein the pressurizing device is further adapted with a fluid leak detector to instantaneously detect radioactive fluid leaks.

44. The catheter of claim 28, wherein the catheter comprises an over-the-wire catheter.

45. The catheter of claim 28, wherein the catheter comprises a rapid exchange catheter.

46. The catheter of claim 28, wherein the catheter comprises a steerable catheter.

47. The catheter of claim 28, wherein the shaft is comprised of a composite construction.

48. The catheter of claim 30, wherein the shaft composite construction comprises a plastic inner tube coaxial with a metal outer layer.

49. The catheter of claim 28, wherein the radioactive fluid emits alpha, beta, or gamma particles.

50. The catheter of claim 28, wherein the reservoir is disposed proximate the shaft distal tip, and the catheter comprises a perfusion catheter.

51. A method of delivering a radioactive source to a target area in a body lumen, comprising:

providing an intravascular catheter, which includes:

an elongated shaft having a shielded section and a treatment section;

the treatment section comprised of a material for enabling radiation from a radioactive source to pass through the treatment section into the target area of the body lumen, the treatment section further includes a reservoir adapted to be expandable and to enable predetermined concentrations of radioactivity in a radioactive source to permeate therethrough;

inserting the catheter shaft in the body lumen until the treatment section is positioned within the target area;

inserting the radioactive source into the treatment section to emit radiation through the treatment section into the target area, the radioactive source being in the form of a radioactive fluid, adapted to flow through the shaft lumen and to expand the reservoir into contact with the target area;

leaving the treatment section in place for a predetermined period of time to enable radiation from the radioactive source to pass therethrough into the target area;

withdrawing the radioactive source from the treatment section; and withdrawing the catheter from the body lumen.

52. The catheter of claim 51, wherein the step of inserting the radiation source comprises applying pressure to the radioactive fluid to initiate flow through the shaft lumen into the reservoir to emit radiation through the treatment section into the target area.

53. A method of delivering a radioactive source to a target area in a body lumen, comprising:

providing an intravascular catheter, which includes:

an elongated shaft having a shielded section and a treatment section;

the elongated shaft includes a lumen extending therethrough and a distal tip;

the elongated shaft further includes a reservoir, disposed proximate the shaft distal tip, in fluid communication with the shaft lumen;

the treatment section comprised of material for enabling radiation from a radioactive source to pass through the treatment section into the target area of a body lumen;

inserting the catheter shaft in the body lumen until the treatment section is positioned within the target area;

inserting the radioactive source into the treatment section to emit radiation through the treatment section into the target area, by applying pressure to the radioactive fluid so as to generate flow thereof through the shaft lumen and to expand the reservoir into contact with the target area;

leaving the treatment section in place for a predetermined period of time to enable radiation from the radioactive source to pass therethrough into the target area;

withdrawing the radioactive source from the treatment section; and withdrawing the catheter from the body lumen.

* * * * *